US006730918B2

(12) United States Patent
Srivastava et al.

(10) Patent No.: US 6,730,918 B2
(45) Date of Patent: May 4, 2004

(54) APPARATUS FOR DETERMINING PAST-SERVICE CONDITIONS AND REMAINING LIFE OF THERMAL BARRIER COATINGS AND COMPONENTS HAVING SUCH COATINGS

(75) Inventors: Alok Mani Srivastava, Niskayuna, NY (US); Anant Achyut Setlur, Niskayuna, NY (US); Holly Ann Comanzo, Niskayuna, NY (US); John William Devitt, Clifton Park, NY (US); James Anthony Ruud, Delmar, NY (US); Luke Nathaniel Brewer, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 179 days.

(21) Appl. No.: 09/683,385

(22) Filed: Dec. 20, 2001

(65) Prior Publication Data

US 2003/0115941 A1 Jun. 26, 2003

(51) Int. Cl.⁷ ................................................. B32B 9/00
(52) U.S. Cl. ............................... 250/458.1; 250/459.1; 356/70
(58) Field of Search ........................... 250/458.1, 459.1, 250/564, 573, 577; 356/70, 320, 326, 435

(56) References Cited

U.S. PATENT DOCUMENTS

| | | | |
|---|---|---|---|
| 4,774,150 A | | 9/1988 | Amano et al. |
| 5,194,910 A | * | 3/1993 | Kirkpatrick et al. .......... 356/70 |
| 5,410,154 A | * | 4/1995 | Broicher et al. ....... 250/339.05 |
| 5,730,528 A | | 3/1998 | Allison et al. |
| 5,780,171 A | * | 7/1998 | Nissley et al. .............. 428/629 |
| 5,793,042 A | * | 8/1998 | Quick .................... 250/339.08 |
| 6,025,078 A | | 2/2000 | Rickerby et al. |
| 6,231,998 B1 | * | 5/2001 | Bowker et al. ............. 428/623 |
| 6,258,467 B1 | | 7/2001 | Subramanian |

FOREIGN PATENT DOCUMENTS

| | | |
|---|---|---|
| EP | 0863396 | 9/1998 |
| WO | 0006796 | 2/2000 |

OTHER PUBLICATIONS

S.W. Allison and G.T. Gillies, "Remote Thermometry with Thermographic Phosphors: Instrumentation and Applications," 68 Rev. Sci. Instrum. 2615 (Jul. 1997).
S. W. Allison et al., "Taking an Engine's Temperature," Mech. Eng. 72 (Jan. 1997).
R. J. Christensen et al., "Nondestructive Evaluation of the Oxidation Stresses through Thermal Barrier Coatings Using Cr3+ Piezospectroscopy," 69 Appl. Phys. Lett. pp. 3754–3756 (Dec. 1996).

* cited by examiner

*Primary Examiner*—Constantine Hannaher
*Assistant Examiner*—Otilia Gabor
(74) *Attorney, Agent, or Firm*—Toan P. Vo; Patrick K. Patnode (57) ABSTRACT

An apparatus for determining past-service conditions and/or remaining useful life of a component of a combustion engine and/or a thermal barrier coating ("TBC") of the component comprises a radiation source that provides the exciting radiation to the TBC to excite a photoluminescent ("PL") material contained therein, a radiation detector for detecting radiation emitted by the PL material, and means for relating a characteristic of an emission spectrum of the PL material to the amount of a crystalline phase in the TBC, thereby inferring the past-service conditions or the remaining useful life of the component or the TBC.

17 Claims, 7 Drawing Sheets

APPARATUS FOR DETERMINING PAST-SERVICE CONDITIONS AND REMAINING LIFE OF THERMAL BARRIER COATINGS AND COMPONENTS HAVING SUCH COATINGS

FEDERAL RESEARCH STATEMENT

This invention was first conceived or reduced to practice in the performance of work under contract DE-FC26-01NT41021 awarded by the United States Department of Energy. The United States of America may have certain rights to this invention.

BACKGROUND OF INVENTION

The present invention relates to thermal barrier coatings, a method, and an apparatus for determination of past-service conditions of coatings and parts and remaining life thereof. In particular, the present invention relates to such a method and an apparatus by a non-destructive optical determination of a particular crystalline phase in a thermal barrier coating.

The constant demand for increased operating temperature in gas turbine engines has necessitated the development of ceramic coating materials that can insulate the turbine components such as turbine blades and vanes from the heat contained in the gas discharged from the combustion chamber for extending the life of such components. These ceramic coatings are known in the art as thermal barrier coatings.

A thermal barrier coating typically comprises at least a layer of a refractory or thermally insulating material such as yttria-stabilized zirconia (or "YSZ") which is zirconia stabilized with, for example, about 6–8 percent by weight of yttria. The refractory material would generally be selected to have a low thermal conductivity such as about 1–3 W/(m) (K), thereby reducing heat transfer to and the temperature experienced by the turbine engine component. The coating may be applied by one of known deposition techniques such as the thermal or plasma spray process or the physical vapor deposition process. A typical thermal barrier coating is a multilayer system comprising three layers. A first so-called bondcoat is applied to the surface of the superalloy of the turbine component. This bondcoat typically comprises a MCrAlY alloy wherein M is nickel, or cobalt, or PtNiAl alloys. The purpose of the bondcoat is to provide a layer which adheres well to the underlying alloy, which provides protection against oxidation of the alloy, and which provides a good base for further coatings. A second intermediate layer or interlayer is applied on the bondcoat. A suitable material for this interlayer is $Al_2O_3$. This material can be formed by oxidizing the surface of the bondcoat to form an oxide layer. The interlayer provides improved adhesion for the final thermal insulating YSZ coating and is not included for a thermal barrier property.

Despite great care taken during manufacture to ensure good adhesion of the thermal barrier coating to the underlying material of the turbine component, thermal cycling during use of such a component eventually leads to spalling of the coating. In addition, erosion of the thermal barrier coating is inevitable over an extended period of use. Such a spalling or erosion would eventually expose the underlying alloy to extreme temperatures that would lead to failure of the component. Therefore, thermal barrier coatings need be inspected frequently for any sign of deterioration. Such an inspection often requires taking the engine component out of service and is time-consuming. A common inspection technique is the visual inspection of the presence or absence of coating. While that method determines when a spall has occurred, it is unable to determine either the degree of deterioration in an intact coating. A method for determining the past-service conditions and remaining life of thermal barrier coatings would be welcome in the art.

Similarly, it is desirable to monitor the condition of the turbine components themselves. In the prior art, it is usual for a destructive evaluation to be performed at each inspection interval for critical components in the hot gas path. In that case, one part is destroyed to produce sections for metallographical examination. The condition of the coatings and base materials are determined from metallographical inspection, and a decision to repair or replace the remaining parts is made from that information.

Better knowledge of the past-service conditions experienced by the turbine components would allow the determination of the remaining life of a part without destructive evaluation. Currently there are few in-situ measurements of hot gas path parts temperatures available. Some physical changes in the phases and structures of the materials of thermal barrier coatings and components occur with exposure to high temperatures. Inspection for changes in phase content is one way to determine past-service conditions.

However, traditional methods of inspection, such as X-ray diffraction and neutron diffraction, require destructive testing and specialized equipment. They are not conducive to being deployed at the site of a gas turbine. In addition, such destructive testing methods necessarily extrapolate the result obtained for one part to the condition of other similarly used parts and, thus, may not provide a true and accurate condition of those parts.

European patent application EP 0863396 A2 discloses a non-destructive measurement method for residual stress proximate an interlayer in a multilayer thermal barrier coating system. This method focuses on detecting compressive stresses that accumulate at the boundary between the interlayer and the outermost thermal barrier coating by detecting the shift in frequency of light emitted by fluorescing chromium ions in the alumina interlayer. However, significant stresses at that boundary may not appear until after the outermost barrier layer has seriously deteriorated. Furthermore, the stresses at the boundary are not useful indicators of the past-service conditions of the component itself. Therefore, such a method is not very useful in timely forewarning a need for repairing or replacing the engine component.

Therefore, there is a continued need to provide a simple non-destructive method for determining the past-service condition of a thermal barrier coating of a component used at high temperature in a turbine engine. It is also very desirable to provide a method by which the remaining useful life of the underlying component may be determined or estimated. Furthermore, it is also very desirable to provide such a method so that maintenance of turbine engine components may be performed only on an as-needed basis rather than on a fixed schedule.

SUMMARY OF INVENTION

The present invention provides a method for determining at least one of past-service conditions and remaining useful life of at least one of a component of a combustion engine and a thermal barrier coating thereof, which component is used in the hot-gas path of the combustion engine. The method of the present invention comprises (1) providing a combustion-engine component comprising a thermal barrier coating that comprises at least one photoluminescent ("PL")

material that can be excited by radiation at a first wavelength range and emits radiation at a second wavelength range different from the first wavelength range in response to the exciting radiation; the radiation emitted at the second wavelength range having a characteristic property that correlates with an amount of a crystalline phase in the thermal barrier coating, which amount increases as the combustion-engine component is exposed to elevated temperatures; (2) directing radiation having the first wavelength range at the thermal barrier coating of the combustion-engine component; (3) measuring the characteristic property of radiation having the second wavelength range; (4) determining the amount of the crystalline phase present in the thermal barrier coating from the characteristic property of radiation having the second wavelength range; and (5) inferring at least one of past-service conditions and remaining useful life of the thermal barrier coating from the amount of the crystalline phase.

According to one aspect of the present invention, the thermal barrier coating comprises yttria-stabilized zirconia.

According to another aspect of the present invention the crystalline phase is the monoclinic phase of zirconia.

The present invention also provides an apparatus for determining at least one of past-service conditions and remaining useful life of at least one of a component of a combustion engine and a thermal barrier coating thereof, which component is used in the hot-gas path of the combustion engine. The apparatus comprises (1) a source of radiation having a first wavelength range directed at the thermal barrier coating that comprises at least one PL material capable of emitting radiation having a second wavelength range in response to an excitation by the radiation having the first wavelength range; (2) a radiation detector being capable of detecting the radiation having the second wavelength range and being disposed to receive and measure a characteristic property thereof; and (3) means for relating the characteristic property of radiation having said second wavelength range to one of an amount of a crystalline phase, past-service conditions, and remaining useful life of the combustion-engine component.

Other features and advantages of the present invention will be apparent from a perusal of the following detailed description of the invention and the accompanying drawings in which the same numerals refer to like elements.

DETAILED DESCRIPTION

As used herein, the term "combustion engine" means any engine that generates work using energy derived from combustion of a fuel. A combustion engine can include components or assemblies of components that convert the energy of the combustion to other forms of energy. Thus, the term "combustion engine" includes turbine engines.

As used herein, the term "elevated temperatures" means temperatures greater than about 700° C.

Figure 1:
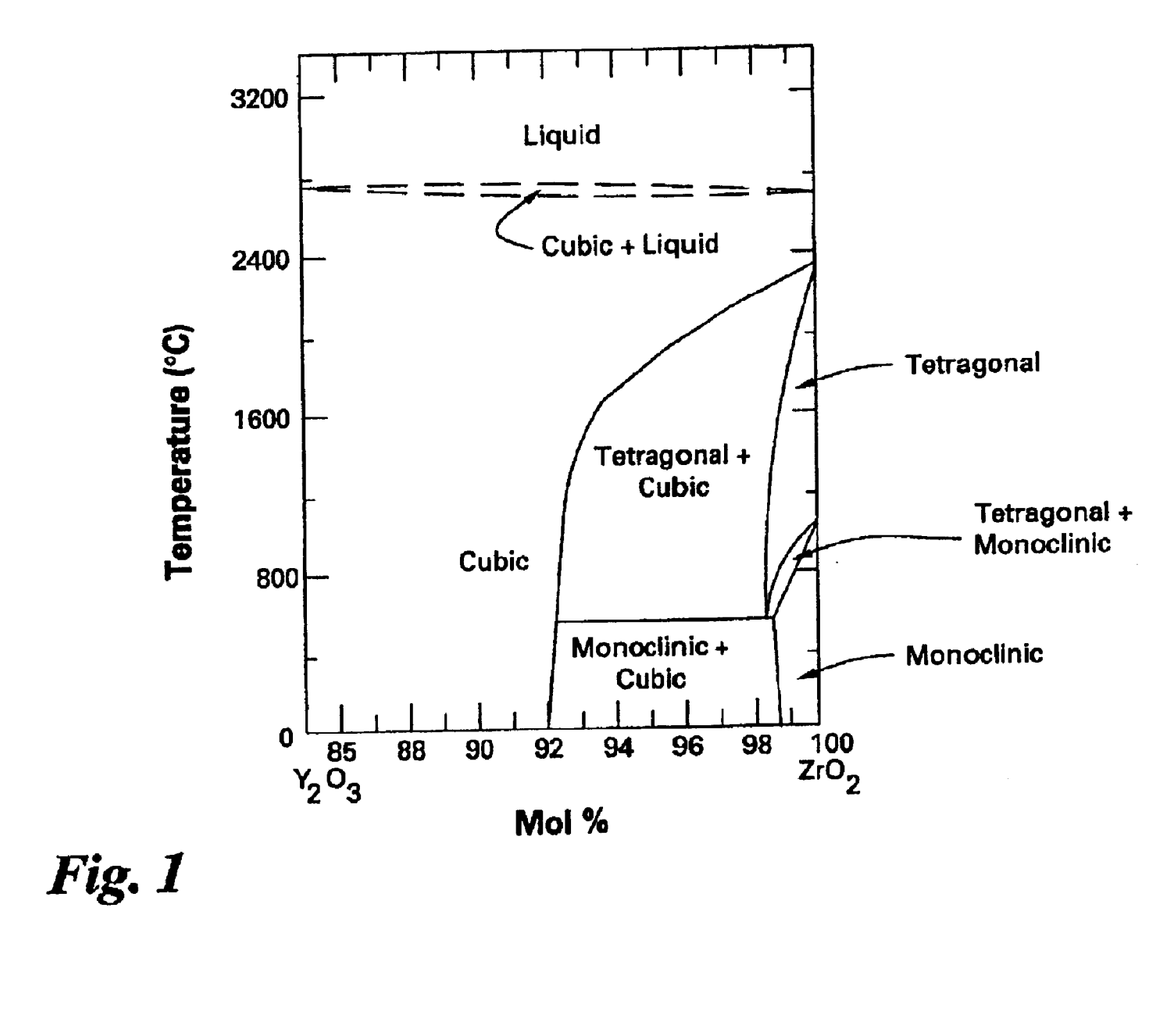
FIG. 1 is the phase diagram showing various phases of zirconia and zirconia stabilized with yttria.

Yttria-stabilized zirconia is a material commonly used as thermal barrier coating ("TBC") for components used in the hot-gas path of gas-turbine engines. This material has many advantages such as high tolerances for thermal shock, low thermal conductivity, and a higher melting point than most oxides. However, one of the limitations of pure zirconia is that it undergoes phase transitions as temperature changes. At temperatures less than 1170° C., the equilibrium phase of zirconia is monoclinic. Between 1170° C. and 2370° C. it is tetragonal, and above 2370° C. it is cubic. The tetragonal-to-monoclinic phase transition occurring as temperature drops to 1170° C. is accompanied by an approximate 3 percent change in volume that causes stresses in the coating and can lead to spallation. FIG. 1 shows that addition of yttria can stabilize zirconia in its cubic or tetragonal phase at temperatures much lower than 1170° C. However, full stabilization to the cubic phase compromises the cyclic thermal fatigue life. Therefore, zirconia is typically partially stabilized with 6–8 percent by weight of yttria ("YPSZ"). The term "yttria-stabilized zirconia" also includes YPSZ. When YPSZ is plasma sprayed in the process of forming the TBC, the molten particles are quenched to form a metastable tetragonal phase having the same composition as the molten YPSZ. This metastable tetragonal phase does not transform immediately into the monoclinic phase when the TBC is cooled rapidly to room temperature. However, during typical use of the engine component that includes extended time at elevated temperatures, the metastable tetragonal phase can undergo a transformation into an equilibrium mixture of the cubic phase and a tetragonal phase that can transform into the monoclinic phase. Since the monoclinic phase has lattice parameters different from those of the cubic and tetragonal phases, the growth of this phase in the TBC would eventually lead to spallation as discussed above. Such a spallation, in turn, would lead to exposure of the underlying alloy material of the engine component to extreme temperatures that would accelerate its failure. As the engine component is exposed to elevated temperatures, it is therefore desirable to determine or monitor the progressive growth of the monoclinic phase in the TBC.

The applicants have discovered that the growth of the monoclinic phase in the TBC can be detected quantitatively and non-destructively by measuring the intensity of a characteristic peak in the emission spectrum of a photoluminescent material incorporated into the TBC. Such a characteristic peak is unique to the presence of the monoclinic phase, and thus can provide an unambiguous determination of past-service thermal conditions of the engine component and/or its remaining useful life before it must be replaced or a new TBC must be applied. The present invention provides a novel method and apparatus for such a determination. Since emission spectrum is measured on the component itself, the data is directly attributed to the condition of the component being tested and the condition of an untested component need not be ambiguously inferred from another destructively tested.

The method of the present invention comprises (1) providing a combustion-engine component comprising a thermal barrier coating that comprises at least one photoluminescent ("PL") material that can be excited by exciting radiation at a first wavelength range and emits radiation at a second wavelength range different from the first wavelength range in response to the exciting radiation; the radiation emitted at the second wavelength range having a characteristic property that correlates with an amount of a crystalline phase in the thermal barrier coating, which amount increases as the combustion-engine component is exposed to elevated temperatures; (2) directing radiation having the first wavelength range at thermal barrier coating of the combustion-engine component; (3) measuring the characteristic property, such as an intensity of a characteristic peak, of radiation having the second wavelength range; (4) determining the amount of the crystalline phase present in the thermal barrier coating from the characteristic property of radiation having the second wavelength range; and (5) inferring at least one of past-service conditions and remaining useful life of the thermal barrier coating from the amount of the crystalline phase.

The present invention also provides a method and apparatus for determining past-service conditions and/or remaining useful life of the thermal barrier coating and the underlying component. Such past-service conditions and/or remaining useful life can be determined reasonably accurately by the amount of the monoclinic phase present in the TBC because such an amount can be correlated to the thermal service history of the component and the expected useful life of a new component similarly constructed. Once the condition and/or the remaining life of the TBC has been determined, the remaining useful life of the engine component also can be determined.

In another embodiment of the present invention, more than one type of activator ions may be incorporated in the photoluminescent host material in the TBC, each type of activator ions being incorporated in a fraction of the thickness of the TBC and each being capable of giving a distinct emission characteristic. As the engine component is exposed to elevated temperature during use, a first type of activator ions can emit a spectrum with a first characteristic that varies with the service time at the elevated temperatures. If the TBC is eroded, for example, because of spallation of an outer portion of the TBC, a second type of activator ions incorporated in a deeper layer of the TBC becomes exposed to excitation radiation and emits a spectrum with a second characteristic. Such a manifestation of difference in spectrum characteristics can provide a measure of an erosion of the TBC and, thus, an estimate of the protection that the remaining potion of the TBC can afford and of the remaining useful life of the TBC and the engine component. In addition, the spectrum having a second characteristic of the second type of activator ions can provide the historical service condition of that portion of the TBC wherein the activator ions of the second type reside. For example, as the engine component is put in service, there is a gradient in the average temperature across the thickness of the TBC. This gradient in average temperature can result in a gradient in the amount of the monoclinic phase across the thickness of the TBC. Therefore, a new peak in the emission spectrum of the second type of activator ions can provide information on this amount of the monoclinic phase in the intermediate portion of the TBC that is exposed after an erosion of the outer portion. The historical service condition, such as the average temperature experienced by the intermediate portion of the TBC can also be determined from such an emission spectrum of the second type of activator ions even in the case in which an erosion of the outer portion of the TBC has not completely or substantially occurred if light pipes have been formed or constructed into the TBC and penetrate the same. In such a case, exiting radiation can be provided to an emitted radiation can be obtained from a deeper portion of the TBC.

A method of the present invention may be implemented on line or off line. In an on-line method, equipment is provided with the engine to carry out the steps of the method. Measurements may be made continuously or at certain desired intervals. In an off-line method, measurements may be made with the cooled-down engine component in place or removed from the engine.

The TBC of an engine component used in the method of the present invention comprises zirconia partially stabilized with yttria in a range from about 6 to about 8 percent by weight. In one aspect of the present invention, the yttria is doped with one of the rare earth-metal ions, such as $Eu^{3+}$ present in europia ($Eu_2O_3$) to render it strongly luminescent in the visible wavelength range in response to an excitation by ultraviolet ("UV") radiation having a wavelength of about 253 nm. As used herein, UV radiation includes radiation having wavelengths from about 100 nm to about 400 nm. Other dopants; for examples, other rare-earth metals, that respond to excitation energy other than UV may be used with yttria. For example, samarium doped in yttria may be excited at about 400 nm to emit in the visible range. Still other oxides may be advantageously used In place of yttrla depending on the circumstances. In such cases, dopants may be chosen to provide emission in a desired wavelength range; for example, In a range that Is most suitable for the chosen radiation detector. Another exemplary dopant is terbium which responds to exciting radiation having wavelength between about 280 nm and about 310 nm and emits with a strong peak at about 543 nm. Still another exemplary dopant is dysprosium which responds to exciting radiation having wavelength about 350 nm and emits with a strong peak at about 572 nm. Erbium is another suitable dopant that responds to exciting radiation having wavelength of about 380 nm and emits with a strong peak at 583 nm. Praseodymium is another suitable dopant that responds to UV exciting radiation having wavelength about 283 nm and emits a strong peak at wavelength about 630 nm. Other rare-earth metal dopants that also may be used are gadolinium, holmium, and thullium.

Typically, an activator ion excited by radiation in one wavelength range emits in another longer wavelength range. For example, when excited in the UV range, typical activator ions emit strongly in the visible-light wavelengths. When excited in the visible-light wavelength range, they typically emit in the longer-wavelength visible range or in the near infrared ("near IR") range.

The present invention also encompasses TBCs that comprise zirconia stabilized with one or more metal oxides other than yttria, such as yttrium aluminum oxide garnet, calcia, magnesia, india, scandia, and/or ytterbia.

Specimens were fabricated, each having a TBC made from oxide powders with nominal composition of 5 weight percent ("wt %") $E_2O_3$/7.6 wt % $Y_2O_3$/87.4 wt % $ZrO_2$ to demonstrate the method and apparatus of the present invention. The specimens were heat-treated in air at a range of temperatures between about 900° C. and about 2000° C. for different times between about 40 minutes and about 1000 hours to change the phase content of the TBC. The fractions of the tetragonal, cubic, and monolithic phases were measured using X-ray diffraction. The coatings had 100% tetragonal phase in the as-fabricated condition before any heat treatment. At higher temperatures and longer times, some of the tetragonal phase is converted to the cubic phase. At the highest temperature and longest time, the monoclinic phase was also observed. The fluorescent spectrum of $Y_2O_3:Eu^{3+}$ was measured for each of the heat-treated specimens. As will be discussed more fully below, new peaks at about 615 nm and about 626 nm were observed in the emission spectrum when the monoclinic phase was present. Thus, the intensity of these peaks can be used to determine the presence and the amount of the monoclinic phase in the novel method of the present invention.

Figure 2:
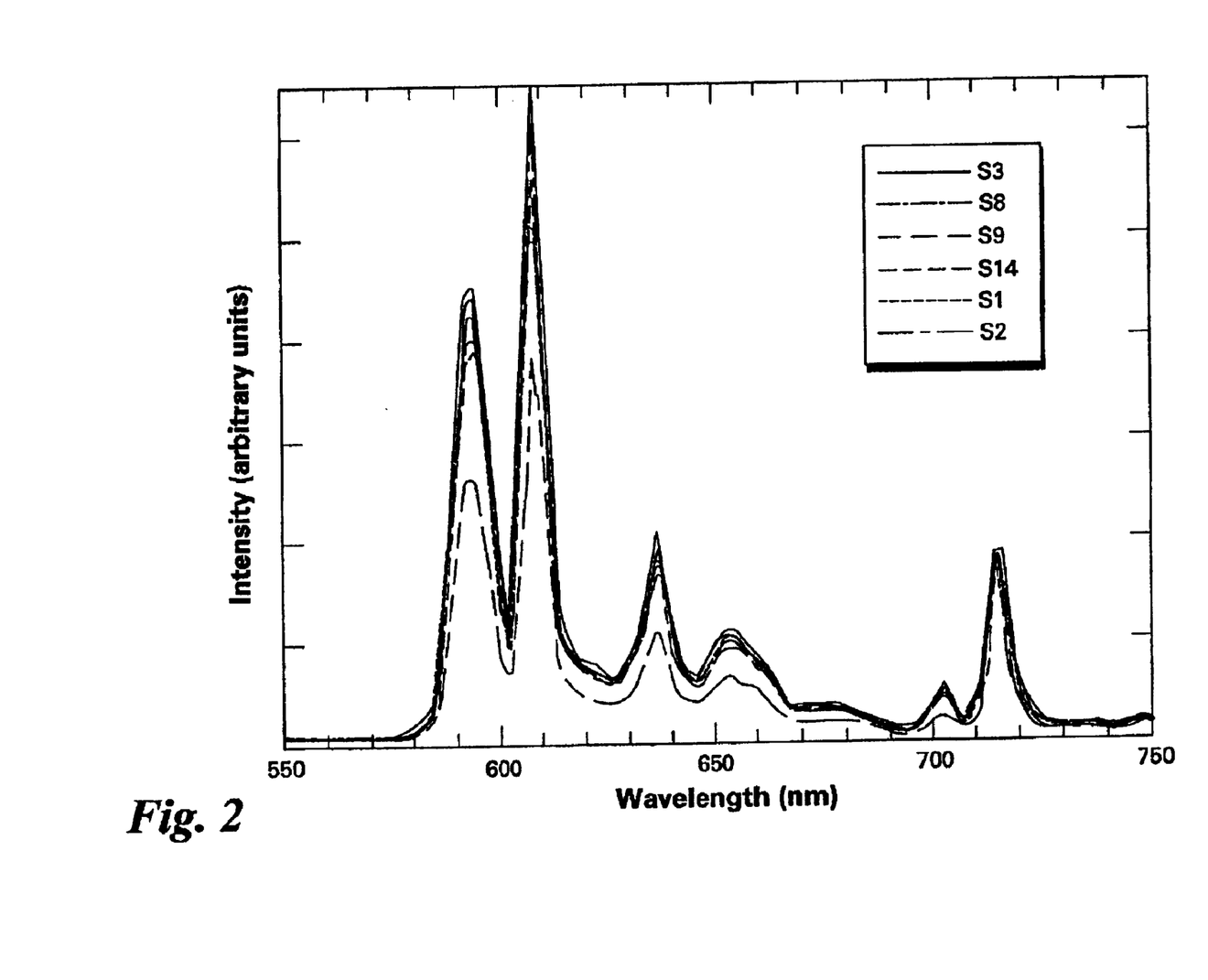
FIG. 2 shows the emission spectra from the PL $Y_2O_3$:$Eu^{3+}$ material in samples of YSZ thermal barrier coatings that have been treated at different temperature to produce only the tetragonal phase.

FIG. 2 shows emission spectra of six specimens (S1, S2, S3, S8, S9, and S14), the TBC of each of which has only the tetragonal phase. Each of the characteristic peaks of each spectrum substantially remains at the same wavelength when only the tetragonal phase is present.

Figure 3:
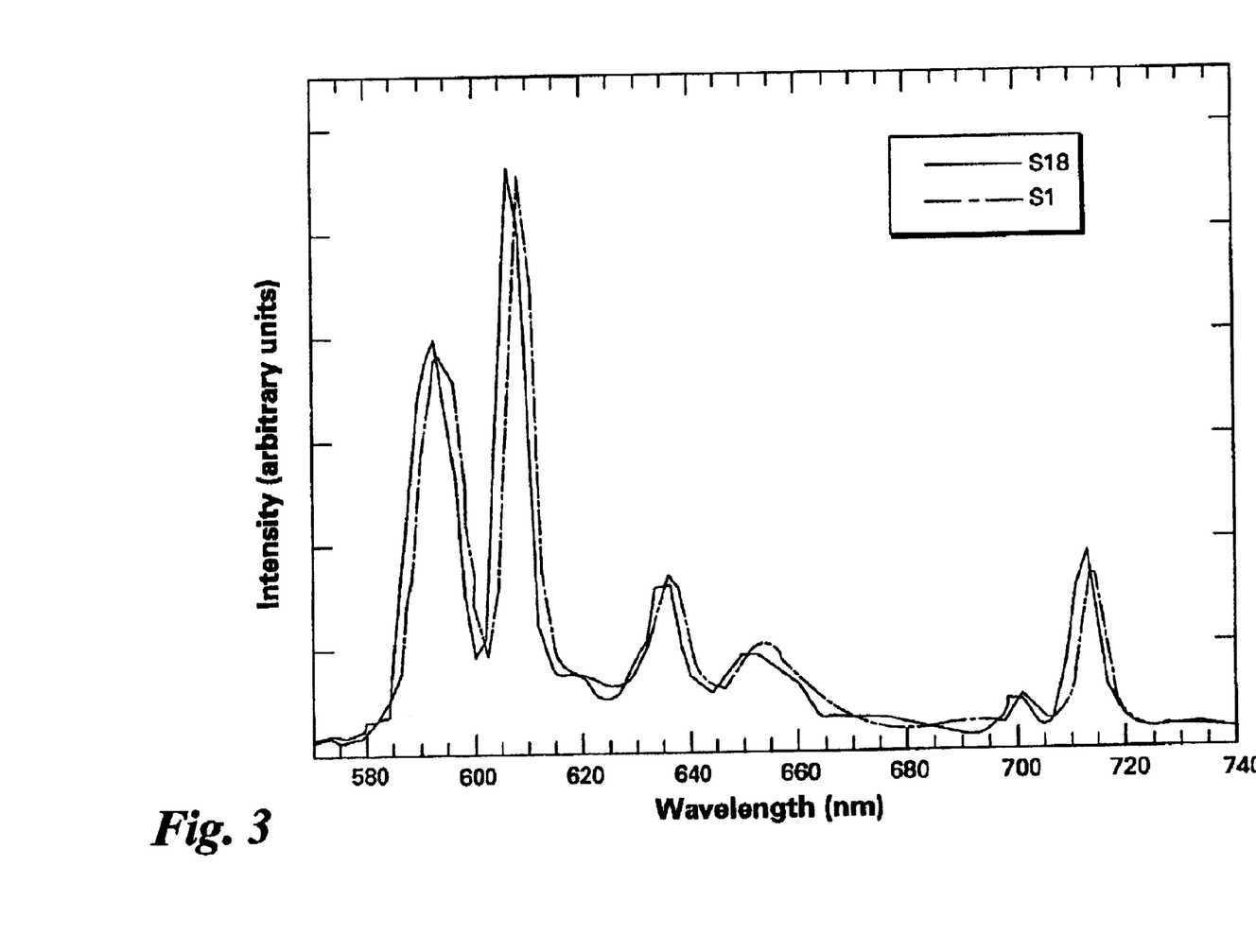
FIG. 3 shows the emission spectra from a sample containing only the tetragonal phase and one containing 36% tetragonal phase and 64% cubic phase.

FIG. 3 shows the spectra of specimen S1 having 100% tetragonal phase and of another specimen S18 having 36% tetragonal phase and 64% cubic phase. Although the peaks of the spectrum of the latter shift to slightly shorter wavelengths they both consist of the same characteristic peaks, the intensity of each peak remaining substantially unchanged.

Figure 4:
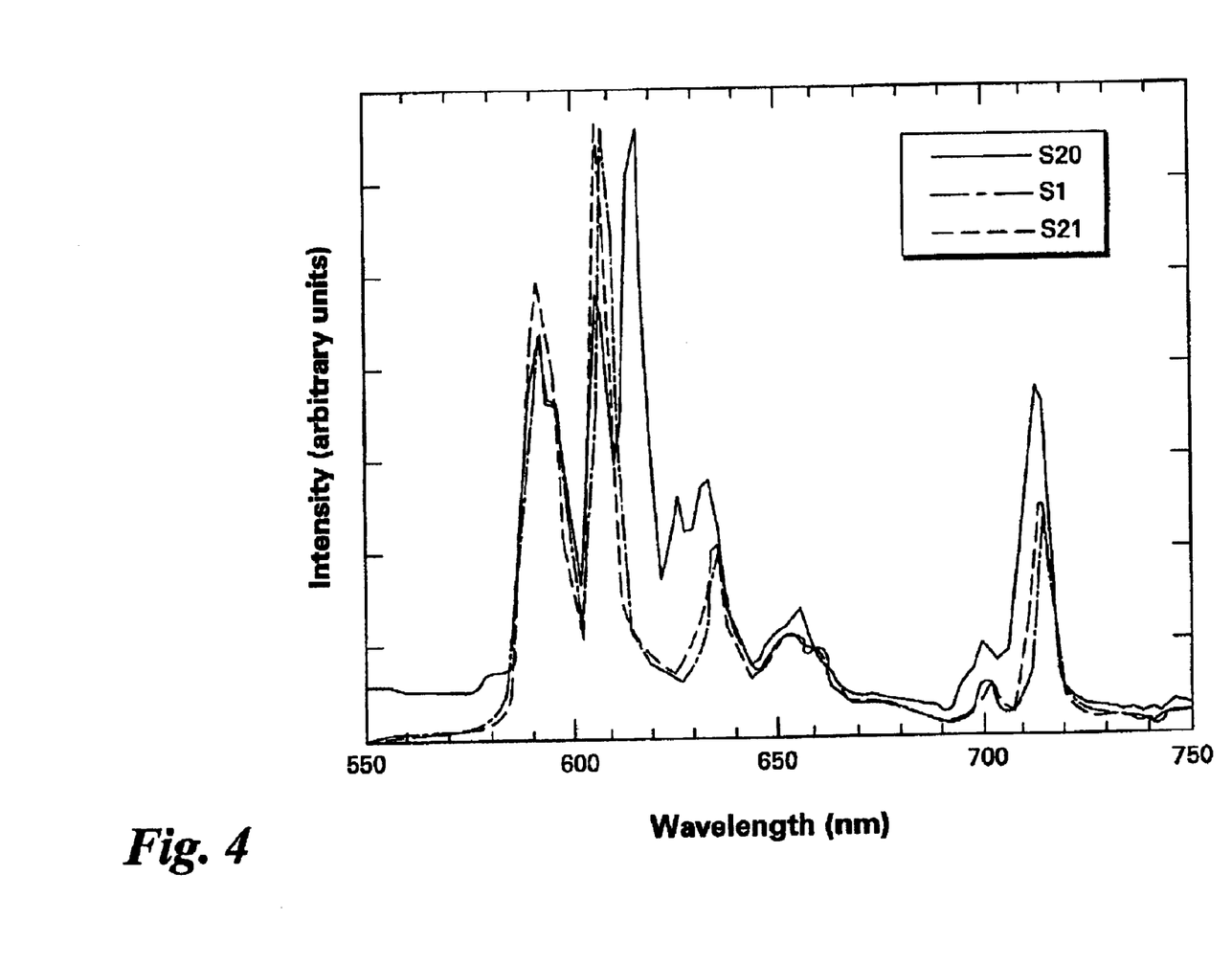
FIG. 4 shows a comparison of the emission spectra of a sample containing 65% cubic phase and 35% monoclinic phase with samples containing only tetragonal and cubic phase.
Figure 5:
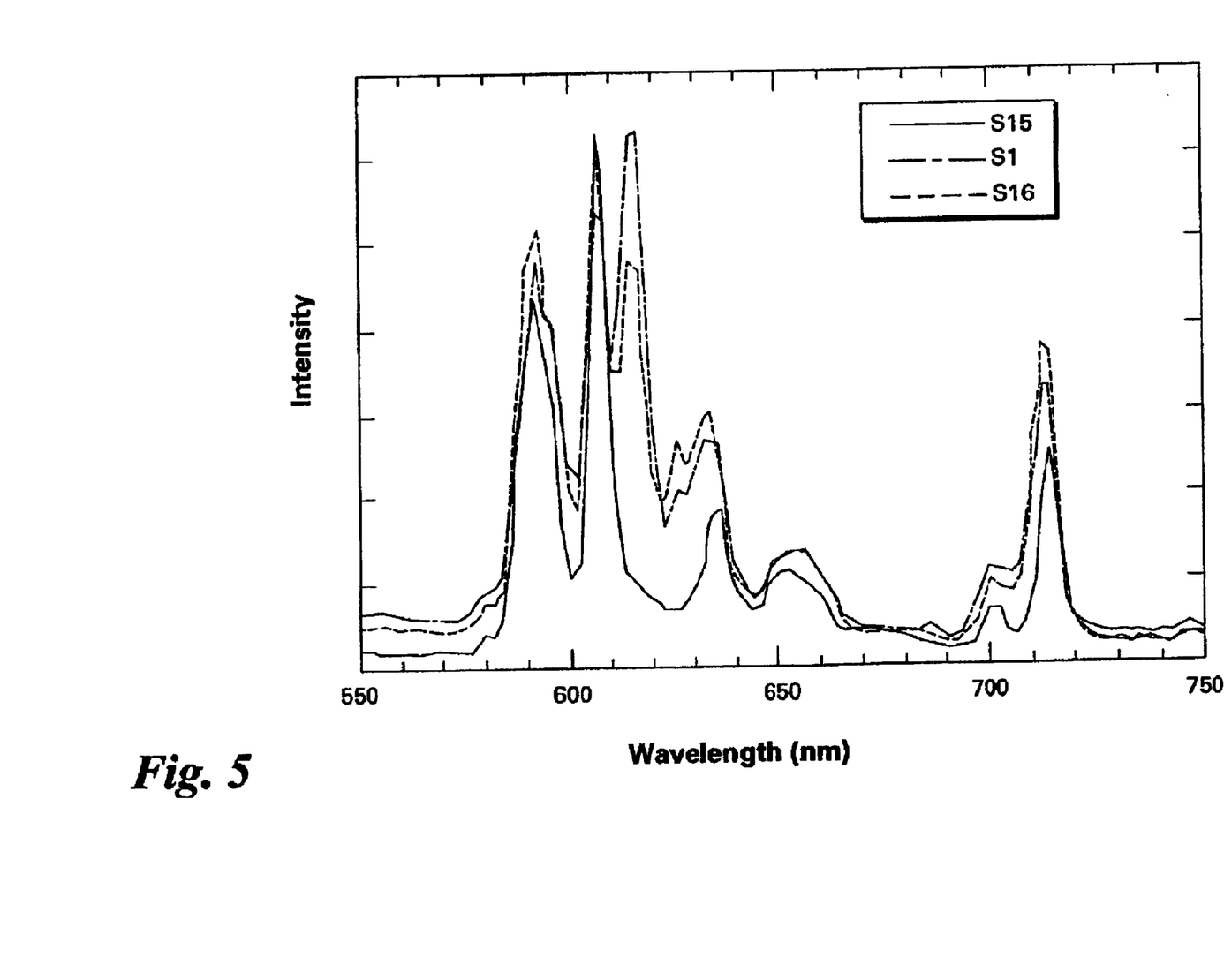
FIG. 5 shows a comparison of the emission spectra of two samples containing different levels of monoclinic phase and containing only tetragonal and cubic phases.
Figure 6:
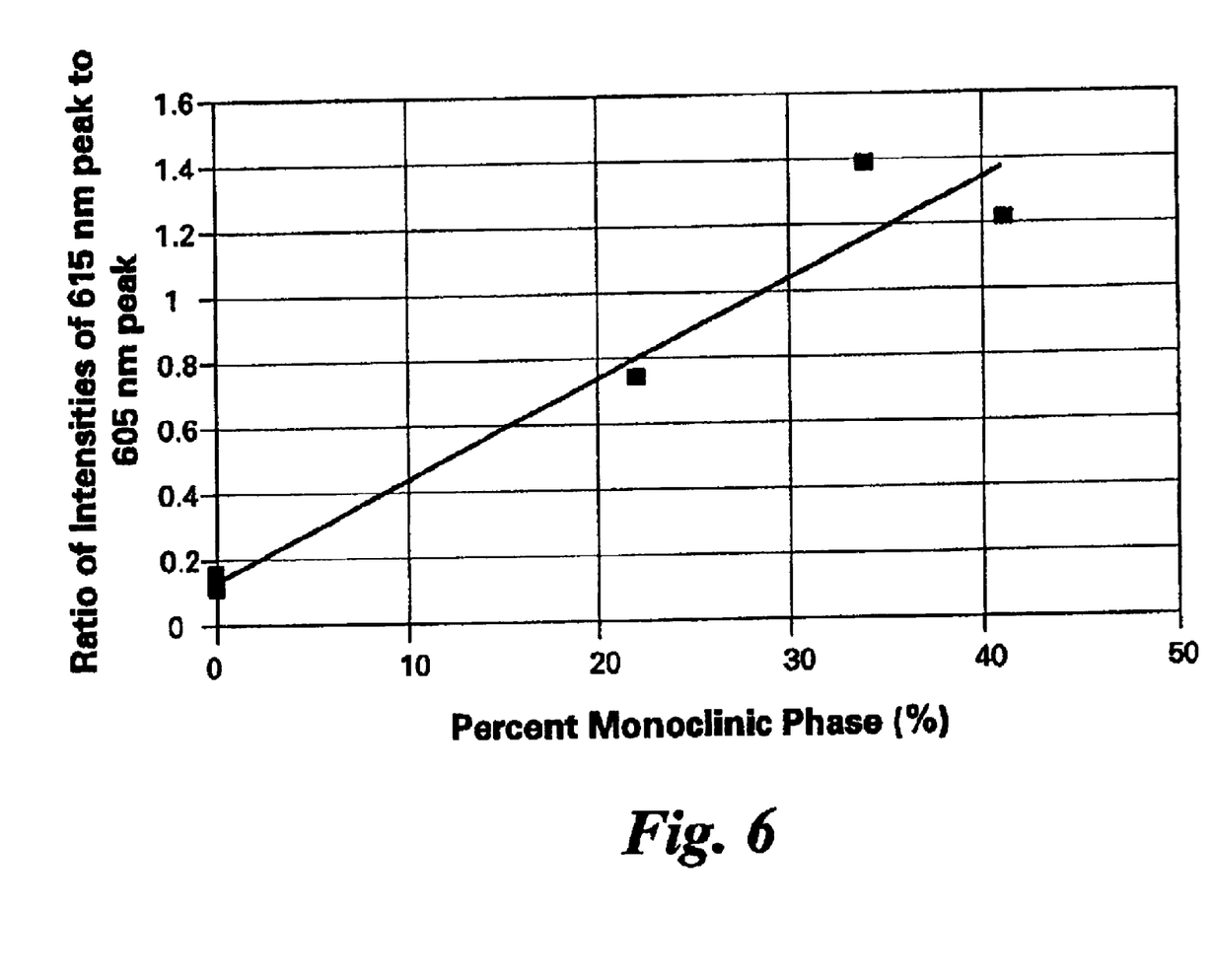
FIG. 6 shows a correlation of the ratio of intensities of peaks at 615 nm and at 605 nm to the amount of monoclinic phase in the thermal barrier coating.

FIG. 4 shows the spectra of specimen S1 having 100% tetragonal phase, specimen S21 having 83% tetragonal phase and 17% cubic phase, and specimen S20 having 65% cubic phase and 35% monoclinic phase. When the monoclinic phase is present a new strong peak at 615 nm and a new weaker peak at about 626 nm appear. FIG. 5 compares the spectra of specimen S15 having 38% tetragonal phase and 62% cubic phase, specimen S16 having 78% cubic phase and 22% monoclinic phase, and specimen S17 having 59% cubic phase and 41% monoclinic phase. As the amount of the monoclinic phase increases, the intensity of the peaks at 615 nm and 626 nm also increases but the intensity of the peak at 605 nm decreases. Therefore, the ratio of the intensity of the peak at 615 nm to that of the peak at 605 nm can be correlated to the amount of the monoclinic phase in the TBC, as is shown in FIG. 6, to provide a novel method for determining this quantity and, thus, for inferring the past-service thermal conditions and/or for estimating the remaining useful life of the engine component. Therefore, the method of the present invention can provide a forewarning of the need to repair or replace the engine component before a serious failure occurs.

Figure 7:
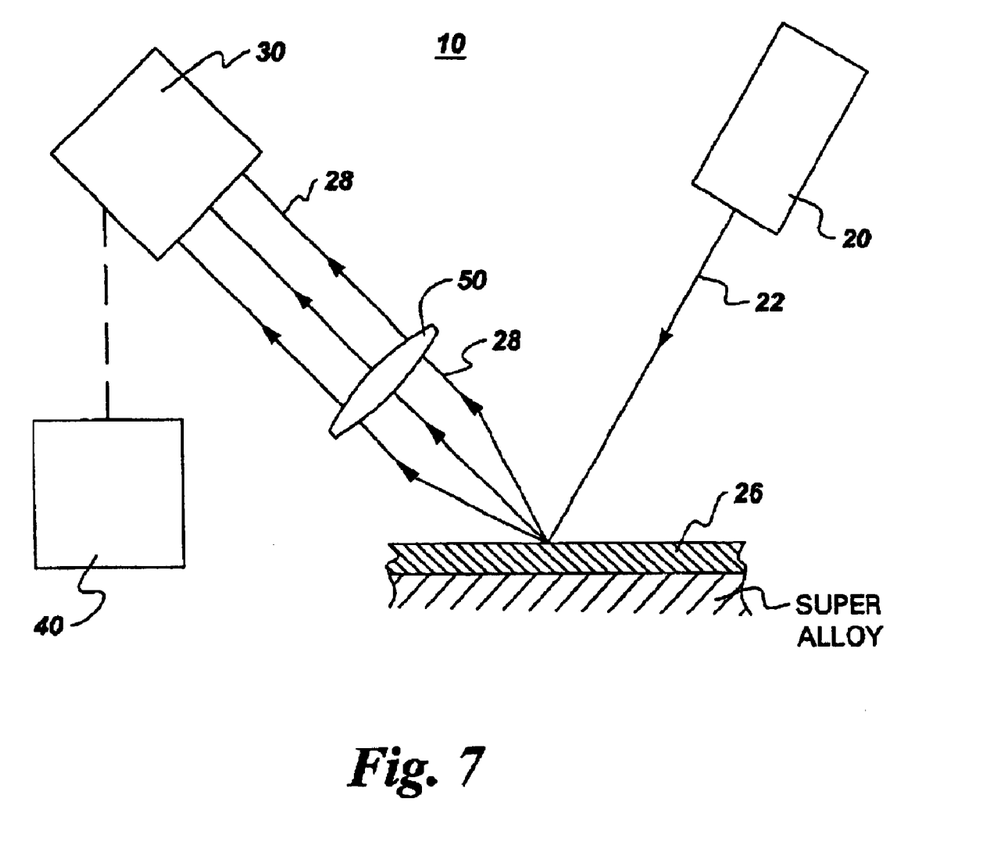
FIG. 7 is a schematic diagram of an apparatus of the present invention.

The present invention also provides an apparatus for determining at least one of past-service conditions and remaining useful life of a thermal barrier coating of a component of a combustion engine, which component is used in the hot-gas path of the combustion engine. FIG. 7 shows a schematic diagram of an apparatus 10 of the present invention. The apparatus 10 comprises (1) a source 20 of radiation 22 having a first wavelength range directed at the thermal barrier coating 26 that comprises at least one PL material capable of emitting radiation 28 having a second wavelength range in response to an excitation by the radiation 22 having the first wavelength range; (2) a radiation detector 30 capable of detecting the radiation 28 having the second wavelength range and being disposed to receive and measure a characteristic property thereof; and (3) means 40 for relating the characteristic property of radiation 28 having said second wavelength range to one of an amount of a crystalline phase, past-service conditions, and remaining useful life of the combustion-engine component.

An apparatus 10 of the present invention can optionally comprise light pipes, such as optical fibers, used to transmit radiation from the radiation source to the TBC and/or to carry the emitted radiation from the TBC to the radiation detector. An apparatus 10 of the present invention can further comprise one or more systems of lenses 50 that focus the radiation emitted from the TBC into an optical fiber and/or one or more systems of optical filters that allow measurement of intensity of light having certain specific wavelengths. In one embodiment of the present invention, the radiation detector is a spectrophotometer.

A past-service condition that can be determined by a method or an apparatus of the present invention may be the extreme temperatures between which or the average temperature at which the engine component has been exposed during service. It may also be the length of time for which the engine component has been in service above a certain temperature.

The turbine engine components that may be inspected by a method or an apparatus of the present invention may be turbine blades, turbine vanes, turbine shrouds, or combustion liners.

The radiation having the first wavelength range may be UV radiation in the range from about 100 nm to about 400 nm or visible light having wavelength in the range up to about 450 nm.

The means for relating the characteristic property of the radiation having the second wavelength range to one of an amount of a crystalline phase, past service conditions, and remaining useful life of the engine component can comprise a general-purpose minicomputer or microcomputer with associated peripheral input/output devices such as analog-to-digital or digital-to-digital converters that can interface between the radiation detector and the computer. Such a computer can be loaded with software that performs the data conversion, correlation, calculation, and outputting. The means for relating can also be analog or digital circuits built specifically for performing the functions noted above. The means for relating can also comprise one or more logical circuits that perform some decision making functions that notify the operator of the engine about the need for repair or replacement of the engine component.

The present invention also provides a TBC disposed directly on a surface of an engine component or on an intervening layer that is in turn disposed on a surface of an engine component. The TBC comprises zirconia and one or more metal oxides that are capable of retarding the propensity of zirconia to form the monoclinic phase. Metal oxides such as yttria, yttrium aluminum oxide garnet, calcia, magnesia, india, scandia, and ytterbia can provide such a capability. The metal oxides are further doped with one or more ions that can fluoresce or luminesce in response to exciting radiation to provide a characteristic property of the monoclinic phase. Rare-earth metal ions may be advantageously used for this purpose. Such a characteristic property may be, for example, a new peak in the emission spectrum of the fluorescing or luminescing metal ions, a shift in the wavelength, or a change in the intensity of a certain peak in the spectrum.

In one aspect of the present invention, the TBC consists essentially of zirconia and at least one metal oxide selected from the group consisting of yttrium aluminum oxide garnet, calcia, magnesia, india, scandia, and ytterbia. The metal oxide is doped with at least one rare-earth metal ion.

While various embodiments are described herein, it will be appreciated from the specification that various combinations of elements, variations, equivalents, or improvements therein may be made by those skilled in the art, and are still within the scope of the invention as defined in the appended claims.

What is claimed is:

1. An apparatus for determining at least one of past-service conditions and remaining useful life of at least one of a component of a combustion engine and a thermal barrier coating thereof, said apparatus comprising:

(1) a source of first radiation having a first wavelength range, said first radiation being directed at said thermal barrier coating that comprises at least one PL material capable of emitting a second radiation having a second wavelength range in response to an excitation by said first radiation;

(2) a radiation detector being capable of detecting said second radiation and being disposed to receive and measure a characteristic property thereof, said characteristic property varying in response to a change in an amount of a crystalline phase in said thermal barrier coating, said change having occurred over a course of past service of said component of said combustion engine; and (3) means for relating said characteristic property of said second radiation to one of said amount of said crystalline phase in said thermal barrier coating, past-service conditions, and remaining useful life of said combustion-engine component;

wherein said crystalline phase being selected from the group consisting of monoclinic phase, tetragonal phase, and cubic phase.

2. The apparatus according to claim 1, wherein said thermal barrier coating comprises zirconia stabilized with at least one material selected from the group consisting of yttria, yttrium aluminum oxide garnet, calcia, magnesia, india, scandia, and ytterbia.

3. The apparatus according to claim 2, wherein said at least one material is doped with at least one rare-earth metal selected from the group consisting of europium, samarium, terbium, dysprosium, erbium, praseodymium, gadolinium, holmium, and thullium.

4. The apparatus according to claim 1, wherein said thermal barrier coating comprises a material selected from the group consisting of yttria-stabilized zirconia and yttria-partially-stabilized zirconia.

5. The apparatus according to claim 4, wherein yttria is present at an amount from about 6 to about 8 weight percent of said thermal barrier coating.

6. The apparatus according to claim 1, wherein said PL material is yttria doped with at least one a rare-earth metal ion.

7. The apparatus according to claim 6, wherein said rare-earth metal is europium.

8. The apparatus according to claim 1, wherein said first wavelength range is an ultraviolet range.

9. The apparatus according to claim 1, wherein said first wavelength range is a visible light less than about 450 nm.

10. The apparatus according to claim 1, wherein said second radiation is a visible light.

11. The apparatus according to claim 1, wherein said second radiation is a near IR radiation.

12. The apparatus according to claim 1, wherein said crystalline phase is a monoclinic phase.

13. The apparatus according to claim 12, wherein said characteristic property is the intensity of a peak at about 615 nm in an emission spectrum.

14. The apparatus according to claim 12, wherein said relating said characteristic property of said second radiation to said amount of said crystalline phase comprises correlating a ratio of intensities of peaks at about 615 nm and about 605 nm with known amount of the crystalline phase.

15. The apparatus according to claim 12, wherein said relating said characteristic property of said second radiation to said past-service conditions comprises correlating a ratio of intensities of peaks at about 615 nm and about 605 nm with known temperatures to which said engine component has been exposed.

16. The apparatus according to claim 12, wherein said relating said characteristic property of said second radiation to said remaining useful life of said engine component comprises correlating a ratio of intensities of peaks at about 615 nm and about 605 nm with a known time to failure of said engine component.

17. The apparatus according to claim 1, wherein said radiation detector is a spectrophotometer.

* * * * *